(12) United States Patent
Ebrecht

(10) Patent No.: US 8,151,625 B2
(45) Date of Patent: Apr. 10, 2012

(54) TEST DEVICE FOR TRIBOLOGICAL EXAMINATION OF MATERIALS

(75) Inventor: Johannes Ebrecht, Eching (DE)

(73) Assignee: Ematec Consulting GmbH, Eching (DE)

( * ) Notice: Subject to any disclaimer, the term of this patent is extended or adjusted under 35 U.S.C. 154(b) by 477 days.

(21) Appl. No.: 12/300,534

(22) PCT Filed: May 10, 2007

(86) PCT No.: PCT/EP2007/004167
§ 371 (c)(1),
(2), (4) Date: Mar. 25, 2009

(87) PCT Pub. No.: WO2007/131709
PCT Pub. Date: Nov. 22, 2007

(65) Prior Publication Data
US 2009/0320555 A1    Dec. 31, 2009

(30) Foreign Application Priority Data
May 12, 2006    (DE) .......................... 10 2006 022 349

(51) Int. Cl.
*G01N 3/56* (2006.01)

(52) U.S. Cl. .................................. 73/9; 73/10

(58) Field of Classification Search .................... 73/9, 10
See application file for complete search history.

(56) References Cited

U.S. PATENT DOCUMENTS

| | | | |
|---|---|---|---|
| 3,041,868 A * | 7/1962 | Marsh et al. ....................... | 73/10 |
| 4,466,271 A | 8/1984 | Geromiller | |
| 4,914,958 A | 4/1990 | van Damme | |
| 5,377,525 A | 1/1995 | Hutchinson et al. | |
| 5,388,442 A | 2/1995 | Kumar et al. | |
| 6,840,082 B2 * | 1/2005 | Evans ................................. | 73/9 |
| 2005/0072208 A1 * | 4/2005 | Domeier ........................... | 73/10 |

FOREIGN PATENT DOCUMENTS

| | | |
|---|---|---|
| DE | 19921760 (A1) | 11/2000 |
| WO | WO 99/41510 | 8/1999 |
| WO | WO 03060487 (A1) | 7/2003 |
| WO | WO 2006/034929 A1 | 4/2006 |
| WO | WO 2006/055994 A1 | 6/2006 |

* cited by examiner

*Primary Examiner* — Hezron E Williams
*Assistant Examiner* — Nathaniel Kolb
(74) *Attorney, Agent, or Firm* — Greer, Burns & Crain, Ltd.

(57) ABSTRACT

A test device for the tribological examination of materials, including at least one first test body that has a first test surface, a drive unit for this at least one first test body that can be driven in oscillating and/or rotating fashion, a measurement device for measuring forces that act on the one hand essentially parallel to the direction of an oscillating introduction of force and/or in the circumferential direction of a rotational introduction of force of the drive unit of the at least one second test body and on the other hand for acquiring the test forces that act between the at least one first test body and the at least one second test body, in addition, a load regulating device is provided that regulates the test force acting between the two test bodies, the prespecified test force being applied to the test bodies with the aid of a decoupled bearing of the drive unit.

19 Claims, 4 Drawing Sheets

TEST DEVICE FOR TRIBOLOGICAL EXAMINATION OF MATERIALS

Figure 1:
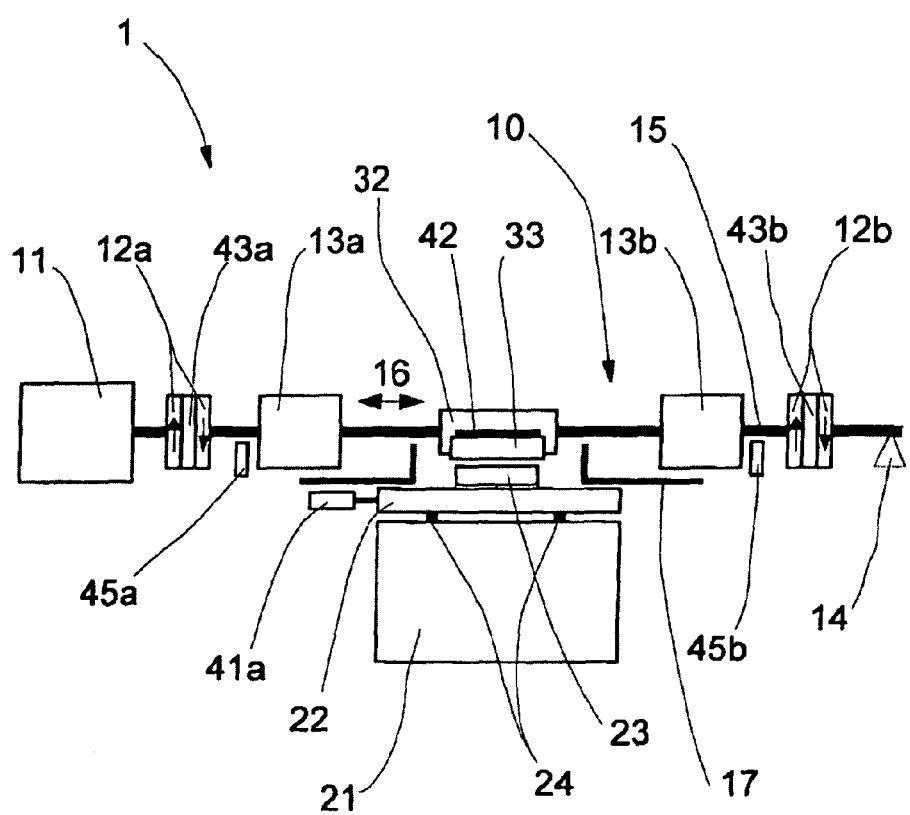

The present invention relates to a test device for carrying out tribological examinations of materials. Both the frictional properties of frictional partners or the properties of a lubricant applied between two frictional partners may be examined. A force is applied to the frictional partners that are to be examined and the frictional force resulting from a relative movement is determined.

As is known, friction arises when the surfaces of two bodies are moved relative to one another with the action of normal forces. The absolute magnitude of the frictional force is a function on the one hand of the applied normal force and on the other hand of the surface properties, as well as the properties of a lubricant that may be situated between the frictional surfaces. The coefficient of friction $\mu$ or z, which indicates the ratio of the normal force to the resulting frictional force, is also a function of these quantities.

For tribological measurements, i.e. in order to examine the friction between materials, test devices are standardly used in which a first test body is moved relative to at least one second test body under a prespecified normal force load. The first test body is connected to a corresponding movement device that executes for example an oscillating or a rotational movement. The second test body is mounted in such a way that the force that is required to hold the second test body during the movement is acquired.

Such systems operate satisfactorily in particular given higher normal forces. In the case of measurements that require a higher degree of precision, however, it has turned out that the measurement result is negatively influenced by the fact that these measurement systems are excited to vibrations. The mounting of the test body on a base element having a high mass inertia and the elastic decoupling of the base element and the test body are both measures that have been introduced in order to reduce vibrations, but they do not achieve this goal satisfactorily. In addition, devices are known that also contain elastic elements in order to reduce the transmission of vibrations. Because, however, in such systems the vibrational energy is essentially damped and is not annihilated, this measure is often insufficient to achieve precise measurement results.

From DE 199 15 288 A1, a device is known for examining frictional conditions in which a test body is mounted on an elastic bearer element made of glass having a plurality of spring arrangements having differing spring rigidities. Here, a soft parallel spring element, provided with stops, for impressing the tangential movement, and a harder plate spring element for impressing the normal force, the latter element acting perpendicular to the two parallel spring elements, are integrated into the elastic element. The device is used primarily to determine small frictional values with a high degree of precision. For larger frictional values and larger applied forces, this device is less suitable.

DE 199 21 760 A1 proposes the acquisition of the vibration of the base element and the preparation of the measurement result in a measurement value processing device in such a way that the base vibrations are taken into account in the evaluation of the measurement result. Therefore, a first sensor device is provided that measures the frictional force, and a second sensor device is provided that measures the vibrations of the base element. However, the improvement in the measurement result in such a test device has to be weighed against the relatively high expense of the construction of the test device, as well as of the evaluation of the measurement results. In addition, the moved system may enter an unstable vibrational state due to the low damping, and the effects of this state may falsify the measurement results in an unacceptable manner.

In tribometers, the normal force acting perpendicular to the test surface is often applied in the form of a static weight that is mounted via a deflecting roller. This is described for example in WO 03/060478. In this patent specification, it is also proposed to use an electromagnetic device, instead of a static weight, to produce the test load. However, a possible embodiment is not described there in more detail.

European laid open print EP 1 607 733 proposes that the test force be applied pneumatically or hydraulically to a spherical test body guided inside a tube. Here, the force between the sphere and the second test body is determined by the supply pressure of the fluid.

The object of the present invention is to make available a test device for tribological examinations whose design makes it possible to impress the test force between the frictional partners that are to be examined in such a way that disturbing vibrations do not arise, so that a precise determination of the frictional values is supported.

According to the present invention, this object is achieved by the subject matter of claim 1. Advantageous developments are the subject matter of the subclaims.

The test device according to the present invention enables the application of a highly precise force without vibrations, thus also enabling a precise measurement of friction. For this purpose, the bearing of the test body system, which is affected by vibration in known tribometers, is decoupled. In known systems, a test body is connected via the machine bed to the base element to which the other test body is fastened, without providing degrees of freedom of the transmitting elements perpendicular to the direction of the flow of force. In this way, the two test bodies form, via their bearings and the machine bed, a system capable of vibration. In order to construct the vibration-optimized tribometer according to the present invention, a decoupled design is therefore provided.

Accordingly, the test device according to the present invention provides that the guide and the bearing of the drive unit be mounted so as to be decoupled from the machine bed in the area of the fastening of the test bodies. For such a bearing, for example hydrodynamic, hydrostatic, aerodynamic, aerostatic, or magnetic bearing types may be used. Magnetic bearings may be both at least partially permanently magnetic, or electromagnetic, or a combination of the two. It is also possible to combine different decoupled bearing types, ensuring the degrees of freedom required for the transmission of force, and to form the test body system in connection with other known bearing types, such as glide bearings or roller bearings. Given the use of magnetic bearings, a shielding of the magnetic effect is preferably to be provided in order to prevent any possible influencing of the tribological point of friction.

The test device according to the present invention provides that the test force be introduced directly by means of the decoupled bearing, thus enabling a largely directed introduction of force, depending on the design of the bearing. This results in expanded possibilities for test setups, such as for example simplified friction measurement on existing components having complex geometries. The direction and magnitude of the force that has to be applied by the decoupled bearing is here a function of the provided test design, the required test force, and the resulting drive unit weight that also has to be accepted by the bearing.

In order to apply a precise test force, and in order to avoid the transmission of vibrations from the machine bed to the test system, the decoupled design according to the present invention provides an elimination of the forces that are not part of the applied test movement. This requires an interruption of the closed flow of these forces between the at least two test bodies. For this purpose, preferably bracing or pre-loading devices are used that enable on the one hand an adjustment of the area of movement of at least one test body in the direction of the application of the test force, thus enabling compensating movements, but that also enable the test movement, which takes place essentially in a plane perpendicular to the introduction of the test force, to be transmitted directly from the drive to the test system.

In order to drive the drive unit, to which at least one first test body is fastened, and that is mounted in the area of the test body fastening in decoupled fashion with respect to possible lateral test forces, if an oscillating movement is to be applied for example a linear motor, a quartz motor, a rotational motor having an eccentric, or a shaker can be used. In order to apply a rotational movement, for example electric motors, quartz motors, or planar motors are suitable. Of course, it is possible to use other suitable drive systems, or also combinations of different drive systems, in order to drive a drive unit.

Preferably, at least one first test body is fixed to the drive unit by a fastening device. Here, a wide variety of shapes of this at least one test body are possible: geometric base elements, such as for example cylinders, cuboids, elements having spherical surfaces, or machine components having a wide variety of shapes. Preferably, the drive unit has different numbers of bearing points relative to the machine bed, as a function of the test design. Depending on the requirements of the test design and the position of bracing devices, these bearing points can be realized by decoupled bearings, or also by bearing points having one or more degrees of freedom. The overall bearing design must preferably ensure a statically determined mounting of the drive unit, which however, as described above, excludes a transmission of disturbing vibrations from the machine bed to the test system. Depending on the desired movement, which can be composed of oscillating and rotational movement elements, a plurality of bearing points are preferably provided in the test device according to the present invention, which can be situated for example in a row, in a plane, or also in space (i.e., in three dimensions).

At least one second test body is mounted fixedly or movably relative to the machine bed. This at least one second test body is preferably fixed to a base element by a fastening device. Here as well, a wide variety of shapes of this test body are possible: geometric base elements, such as cylinders or cuboids, enabling for example a point-surface contact, a line-surface contact, or a surface-surface contact. Likewise, for example contact shapes that are specific to existing machine components may also be examined.

In another preferred specific embodiment, the base element on which the at least one second test body is fastened is driven. Here as well, in addition to other suitable drive systems, linear motors, quartz motors, rotational motors with or without eccentric, planar motors, shakers, or combinations of these drive systems are possible for use as the drive unit.

In order to ensure a simple design of the test device, compensating elements are preferably provided on the base element to which the at least one second test body is fixed by a fastening device, said compensating elements ensuring absolute parallelness of the test body surfaces. Preferably, these compensating elements, or additional devices, also compensate height differences that can occur for example due to wear. Spring plates or similar auxiliary devices may be used as compensating elements in a known manner.

The test device according to the present invention also preferably comprises a measurement device that is provided in order to acquire the required measurement values. What is fundamental here is the measurement of the resulting frictional forces that, for example given an oscillating movement, act between the test bodies essentially parallel to the direction of the introduction of force of the drive unit, or that given a rotating movement, act in the circumferential direction of the rotating test body. In order to measure the frictional force on the preferably stationary test body, in the case of a translational drive movement at least one force sensor is used that may function for example piezoelectronically, by means of strain gauges, or by some other suitable measurement principle. Given a rotational drive movement, the resulting frictional force is also acquired at the preferably stationary test body in the circumferential direction of the rotation, using at least one force sensor. If the movement is a mixture of rotational and translational movement, preferably a plurality of force sensors are to be situated such that the measurement device picks LIP the resulting characteristic frictional forces. The named types of force sensors may also be used to measure rotational forces or forces having translational and rotational components.

In addition, the measurement device is also used to determine the test force applied between the frictional surfaces. For this purpose, a force sensor is preferably situated on a fastening device of a test body in order to measure the normal force. The first and also the second fastening device are suitable for this purpose. The arrangement of the force sensors is determined dependent at least on the test system, the direction and movement of the introduction of force, and accessibility. For the force measurement, here as well sensors are suitable that may function piezoelectronically, by means of strain gauges, or according to some other suitable measurement principle. If, due to the geometric shape of the test body or of the test system (e.g. a four-ball system) the test force does not act in the direction of the normal force, the test force may be measured for example using a sensor that is situated relative to the direction of force. Alternatively, the test force resulting from the normal force may preferably be calculated in the computing device allocated to the test device.

In order to regulate the test force that is applied to the test system by means of the segments of the drive unit guided in the decoupled bearings, preferably the position of the mounted segments is also acquired by the measurement device and is further processed in the machine control unit, and in particular in the load regulating device. For the position measurement, the measurement device therefore preferably comprises position sensors that correspond in their number and situation to the design of the decoupled bearing, said sensors acquiring the position of the drive unit with sufficient precision.

These sensors acquire the position of the drive unit for example by means of an inductive, capacitive, or optical function. Of course, it is also possible to use position sensors that operate using other suitable measurement principles. If the cross-section of the segment of the drive unit guided in the decoupled bearing is for example circular, then, preferably, two sensors can be situated at intervals of 180° around the drive unit segment, or three sensors can be situated at intervals of 120°, or four sensors can be situated at intervals of 90°. Such an arrangement is preferably useful if an equal number of bearing functional units, such as electromagnets in the case of magnetic bearings, are arranged in the same way. This enables a direct allocation of the acquired position values to the functional units.

In a preferred specific embodiment of the test device according to the present invention, the measurement device is also used to acquire a large number of additional method parameters. These method parameters include for example the operating data of the drives of the test device or the positioning and adjustment of the test bodies to one another. Preferably, an additional measurement also takes place of resulting forces, for example in the bracing devices, as well as an acquisition of vibrations and similar disturbing quantities that may be introduced into the machine bed or into the drive device. Preferably, the measurement device according to the present invention comprises a plurality of sensors that acquire the parameters of the test environment. The most important of these characteristic values that influence the test result are temperature, air humidity, and air pressure. However, it may also be required to use additional sensors allocated to the measurement device to acquire additional characteristic values.

Various control designs may be used to control the test device according to the present invention. The preferred specific embodiment operates for example using a thyristor control device. Independent of the control design, the computing device contains at least one microprocessor that is controlled by a program that is stored in a storage device allocated to the microprocessor. This storage device may be divided into arbitrarily many storage areas, which may differ from one another. From the read-in data of the measurement device, the microprocessor derives the control signals for the execution of the tribological examination. Here, the load regulating device regulates, as a functional unit of the microprocessor, the test force that is applied between the test surfaces via the decoupled bearing of the drive unit.

All data of the measurement device, that is, the measurement values of all sensors provided on the test device, are preferably read into this microprocessor. In particular, the measurement values of the force sensors that acquire the force between the test bodies and/or the position values of the segments of the drive device in the decoupled bearings are used as input quantities for the load regulating device. Using these data, the load regulating device preferably regulates the normal force acting on the test bodies precisely to the pre-specified value.

All measurement values of the measurement device are preferably read into the storage device of the microprocessor. The data of the sensors that record the resulting frictional forces as well as the test conditions are preferably provided for further evaluation in the storage device. The microprocessor preferably comprises electrical interfaces to which there may be connected an evaluation device, such as a PC or a device-specific operating unit that has an input unit, such as a keyboard, and a display device. The connection can take place via a cable or also wirelessly, preferably via wireless LAN, an infrared interface, or Bluetooth technology. In this way, the measurement results of the test device according to the present invention can be further processed using any suitable software present for example on a PC, on a device-specific operating unit, or on some other evaluation device.

Further advantages, features, and possible applications of the present invention result from the following description in combination with the Figures.

Figure 2:
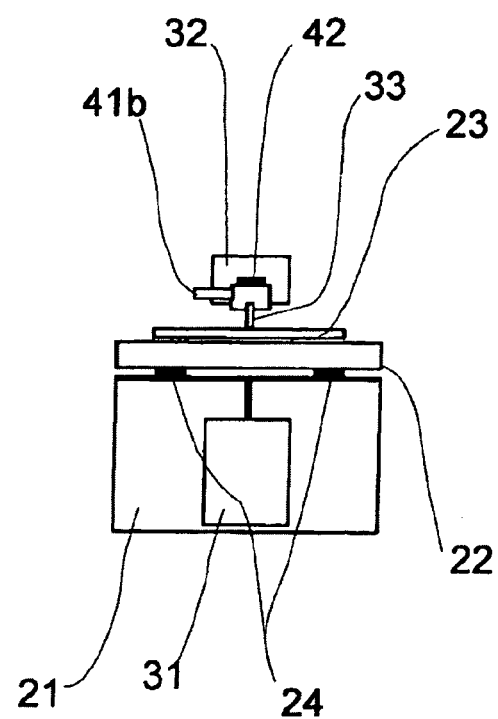
Figure 3:
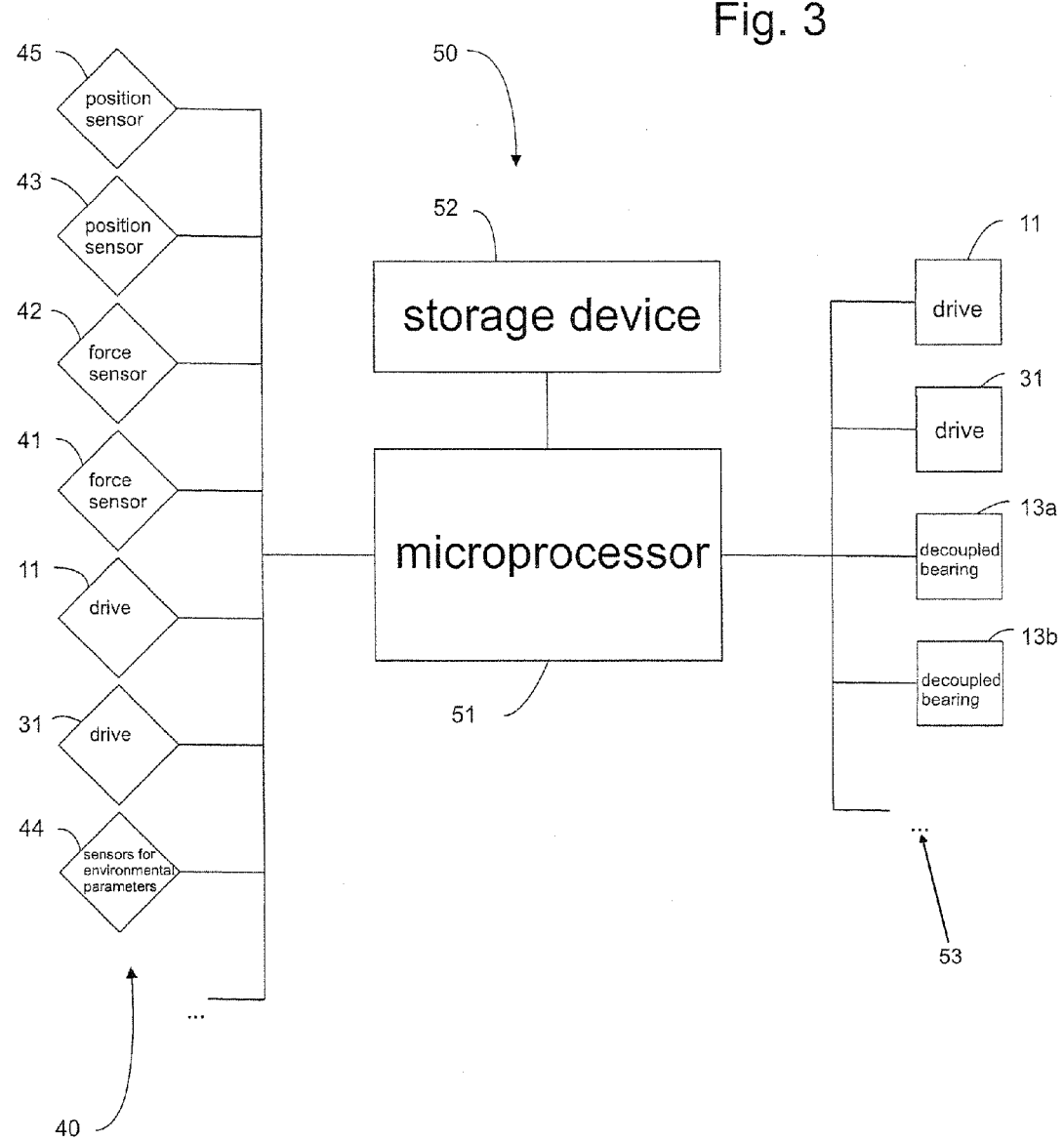
Figure 4:
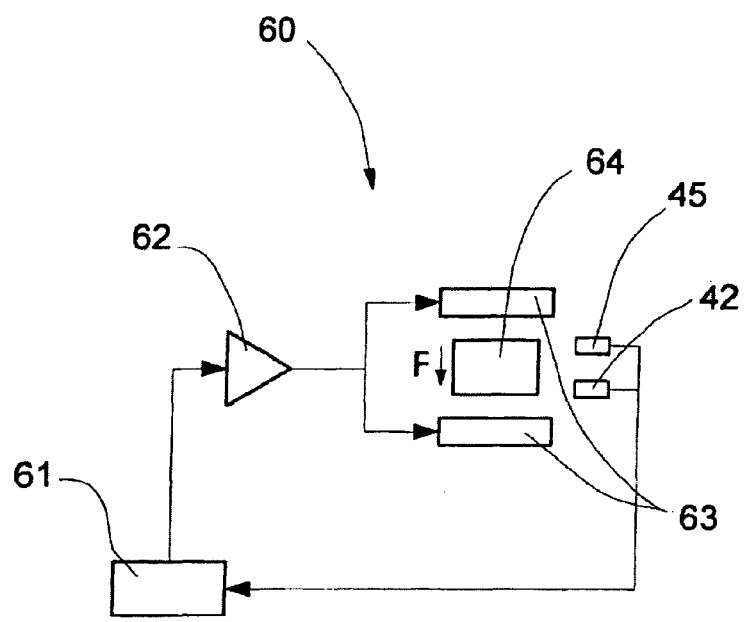

FIG. 1 shows the schematic design of a test device according to the present invention having an oscillating relative movement between the test bodies, FIG. 2 shows the schematic construction of a base element having a rotational drive, FIG. 3 shows a schematic block diagram of the computing device, and FIG. 4 shows a schematic block diagram of the control circuit of the load regulating device.

FIG. 1 shows the schematic design of a test device 1 according to the present invention, in which a first test body that is fastened to a drive unit applies a frictional force to a second test body with an oscillating movement. Drive unit 10 comprises drive shaft 15 which extends from oscillating drive 11 (shown at left) to bearing 14 (shown at right) of the drive unit. Approximately in the center of drive shaft 15, which moves in oscillating fashion in the direction of arrow 16, first fastening device 32 for first test body 33 is fixed to drive shaft 15. On both sides of this first fastening device 32, bearings 13a and 13b, each decoupled, are situated on the circumference of drive shaft 15; in the exemplary embodiment, these bearings are realized as magnetic bearings.

On both sides, a shielding 17 is situated between the tribological point of friction and magnetic bearings 13; this shielding prevents a magnetic effect on the frictional examination. Bracing devices 12a and 12b are also situated on both sides of the bearings, between bearing 13a and oscillating drive 11, or between bearing 13b and mount 14 of the drive unit. These bracing devices enable an adjustment of the vertical decree of freedom of the drive unit relative to the machine bed. On first fastening device 32 there is situated a force sensor 42 that acquires the normal force impressed between the two test bodies 23 and 33.

Base element 21 is situated on the machine bed (not shown in FIG. 1). A second fastening device 22 to which second test body 23 is fixed is allocated to base element 21. Base element 21 shown here, with second fastening device 22, represents a static bearer unit without a drive. Between base element 21 and second fastening device 22 there are situated compensating element 24 that ensure the parallelness of the surfaces of the test bodies, and that compensate height differences that may arise for example in case of wear.

A force sensor 41a for acquiring the frictional forces that results from the translational movement of oscillating drive 11 is allocated to second fastening device 22. The position of second test body 23 is recorded via position sensors 45a and 45b, which are allocated to die decoupled bearing point, and via position sensors 43a and 43b, which are situated on the two clamping units 12a and 12b.

FIG. 2 shows the schematic construction of another test system for a tribological examination. Second fastening device 22 is situated on base element 21, to which a rotational drive 31 is allocated. In the exemplary embodiment, a disk-shaped second test body 23 is fixed on the depicted fastening device 22. A cylindrical test body 33 is fixed to first fastening device 32. The depicted arrangement is known as a pin-surface arrangement. Drive shaft 15, which in this exemplary embodiment is not driven but impresses the test force applied by means of the decoupled bearing, is not shown in FIG. 2.

The measurement device of the test design shown in FIG. 2 comprises a rotational force sensor 41b that is situated on first fastening device 32 in order to acquire the rotational frictional force. In order to measure the normal force impressed between the two test bodies, force sensor 42 is situated on first fastening device 32.

FIG. 3 shows a schematic block diagram of an example of a computing device 50 of the test device according to the present invention. The measurement values acquired by force sensors 41 and 42 and by position sensors 45 and 43 are used together with the functional values of drives 11 and 31, as well as with additional recorded measurement values acquired by sensors for environmental parameters 44, as input values for microprocessor 51. From the read-in data, microprocessor 51 calculates the control values for drives 11 and 31 for the precise controlling of the movement between the test bodies provided during the execution of the test. Here, microprocessor 51 also includes the functionality of a load regulating device 53 that regulates decoupled bearings 13a and 13b in such a way that they transmit a precise test force onto drive shaft 15, thus impressing this force between test bodies 23 and 33. The data processed in microprocessor 51 is stored together with the values acquired by measurement-device 40 in storage device 52 for further evaluation.

FIG. 4 shows a schematic block diagram of an example of a control circuit 60 of a load regulating device. The purpose of the load regulating device is to apply a test force to drive shaft 15, and thus between the two test bodies 23 and 33, that is prespecified in its direction and magnitude. The regulation is responsible for holding drive shaft 15 in a specified, loaded position perpendicular to the test surface. Here, the sum of all forces acting on first test body 33 in the provided direction must correspond to the magnitude of the required test force. For this purpose, the position of shaft segment 64 is acquired via position sensors 45. The magnitude of the force applied by the bearing is recorded by force sensor 42. These values determine the actual situation in the bearing as input values of regulator 61.

Electromagnets 63 are situated on the periphery of shaft segment 64 of the drive device. Via the input values of sensors 42 and 45, regulator 61 controls the current in electromagnets 63 via power amplifier 62 in such a way that the desired test force is set. The active regulation thus achieves a stable state of suspension.

The invention claimed is:

1. A test device for the tribological examination of materials, comprising:
   at least one first test body that has a first test surface;
   a drive unit for said at least one first test body that is driven in oscillating fashion;
   at least one second test body being arranged on a machine bed;
   a measurement device for measuring forces that act on the one hand essentially parallel to the direction of an oscillating introduction of force of the drive unit of the at least one second test body and on the other hand for acquiring a test force that acts between the at least one first test body and the at least one second test body; and
   a load regulating device that regulates the test force acting between the first and second test bodies, the test force being applied to the test bodies with the aid of a bearing of the drive unit being mechanically decoupled from the machine bed.

2. The test device as recited in claim 1, wherein the functional principle of the decoupled bearing is selected from a group including magnetic, hydrostatic, hydrodynamic, aerostatic, and aerodynamic effects.

3. The test device as recited in claim 1, wherein the bearing of the drive unit is supported by at least two bearing points.

4. The test device as recited in claim 1, further comprising bracing devices that transmit the test movement directly from the drive unit to a test system made of the first and second test bodies, thus enabling compensating movements in the direction of the introduction of the test force.

5. The test device as recited claim 1, wherein the base element on which the at least one second test body is fastened is driven in accordance with a test movement.

6. The test device as recited in claim 1, wherein the direction and magnitude of the force that is to be applied to a system made of the first and second test bodies are adjustable.

7. The test device as recited in claim 1, wherein the tribological frictional point is shielded with respect to a possible influencing by the decoupled bearing of the drive unit.

8. The test device as recited in claim 7, further comprising a test body bearing including compensating elements that ensure the parallelness of the test surfaces, and that compensate differences in height that may arise for example in case of wear.

9. The test device as recited in claim 1, wherein the test device is used to examine a medium introduced between the test bodies.

10. The test device as recited in claim 1, wherein the measurement device comprises sensors that are situated in the area of the fastening of the test bodies and that are used to measure the resulting frictional forces.

11. The test device as recited in claim 1, wherein the measurement device has at least one sensor that is used to acquire the normal force that is applied to a test body system made of the first and second test bodies via the drive unit.

12. The test device as recited in claim 1, wherein the measurement device acquires a multiplicity of method parameters of the execution of the examination.

13. The test device as recited in claim 1, wherein the measurement device has in the area of the bearing of the drive unit at least one sensor that is used to determine the position of the drive unit.

14. The test device as recited in claim 13, further comprising a computing device having at least one microprocessor that is controlled by a program that is stored in a storage device allocated to the microprocessor.

15. The test device as recited in claim 14, wherein the measurement values of the measurement device are forwarded to the microprocessor as input values.

16. The test device as recited in claim 14, wherein the microprocessor unit comprises a load regulating device that regulates the test force.

17. The test device as recited in claim 14, wherein the microprocessor comprises interfaces to which an evaluation device or a device-specific operating unit can be connected.

18. A test device for the tribological examination of materials, comprising:
   at least one first test body that has a first test surface;
   a drive unit for this at least one first test body that is driven in oscillating fashion;
   at least one second test body being arranged on a machine bed;
   a measurement device for measuring forces that act on the one hand essentially parallel to the direction of an oscillating introduction of force of the drive unit of the at least one second test body and on the other hand for acquiring the test forces that act between the at least one first test body and the at least one second test body; and
   a load regulating device that regulates the test force acting between the first and second test bodies, the test force being applied to the test bodies with the aid of a magnet bearing of the drive unit such that the drive unit is mechanically decoupled from the machine bed.

19. A test device for the tribological examination of materials, comprising:
   at least one first test body that has a first test surface;
   a drive unit for this at least one first test body that is driven in oscillating fashion;
   at least one second test body being arranged on a machine bed;

a measurement device for measuring forces that act on the one hand essentially parallel to the direction of an oscillating introduction of force of the drive unit of the at least one second test body and on the other hand for acquiring the test forces that act between the at least one first test body and the at least one second test body; and a load regulating device that regulates the test force acting between the first and second test bodies, the test force being applied to the test bodies with the aid of a bearing of the drive unit being mechanically decoupled from the machine bed, wherein the measurement device has in the area of the bearing of the drive unit at least one sensor that is used to determine the position of the drive unit, the determined position of the drive unit being further processed in the load regulating device.

* * * * *